(12) United States Patent
Guenschel et al.

(10) Patent No.: US 10,466,197 B2
(45) Date of Patent: Nov. 5, 2019

(54) COMPONENT PART HAVING A MECS COMPONENT ON A MOUNTING CARRIER

(71) Applicant: Robert Bosch GmbH, Stuttgart (DE)

(72) Inventors: Roland Guenschel, Wannweil (DE); Harald Guenschel, Gerach (DE); Lothar Diehl, Gemmrigheim (DE); Gerhard Schneider, Pettstadt (DE)

(73) Assignee: Robert Bosch GmbH, Stuttgart (DE)

( * ) Notice: Subject to any disclaimer, the term of this patent is extended or adjusted under 35 U.S.C. 154(b) by 795 days.

(21) Appl. No.: 15/156,856

(22) Filed: May 17, 2016

(65) Prior Publication Data

US 2016/0341689 A1    Nov. 24, 2016

(30) Foreign Application Priority Data

May 21, 2015   (DE) .................. 10 2015 209 267

(51) Int. Cl.
   *G01N 27/407*   (2006.01)
   *B81C 1/00*   (2006.01)

(52) U.S. Cl.
   CPC ..... *G01N 27/4078* (2013.01); *B81C 1/00253* (2013.01); *B81B 2201/0214* (2013.01); *B81B 2203/0127* (2013.01); *B81C 2201/019* (2013.01); *G01N 27/4071* (2013.01)

(58) Field of Classification Search
   CPC ............ G01N 27/4078; G01N 27/4071; B81C 1/00253; B81C 2201/019; B81C 2201/0214; B81B 2203/0127
   See application file for complete search history.

(56) References Cited

U.S. PATENT DOCUMENTS

| | | | |
|---|---|---|---|
| 2002/0023838 A1* | 2/2002 | Schneider | G01N 27/4071 204/429 |
| 2005/0178208 A1* | 8/2005 | Benzel | G01L 9/0055 73/715 |
| 2011/0073969 A1* | 3/2011 | Benzel | B81B 7/007 257/419 |

* cited by examiner

Primary Examiner — J. Christopher Ball
(74) Attorney, Agent, or Firm — Norton Rose Fulbright US LLP; Gerard Messina

(57) ABSTRACT

A packaging technology for MECS components, which allows the realization of extremely robust components which are resistant to high temperatures and media. Such a component includes at least one micro-electrochemical sensor (MECS) component having a diaphragm, which is developed in a layer construction on the substrate of the component and spans an opening in the substrate rear side, and a carrier for the mounting and electrical contacting of the MECS component on an application circuit board. The MECS component is bonded to the carrier in flip chip technology, so that a hermetically tight mechanical connection between the top surface of the MECS component and the carrier surface exists at least in one connection region, and an electric connection between the MECS component and the carrier exists in at least one contact area.

11 Claims, 1 Drawing Sheet

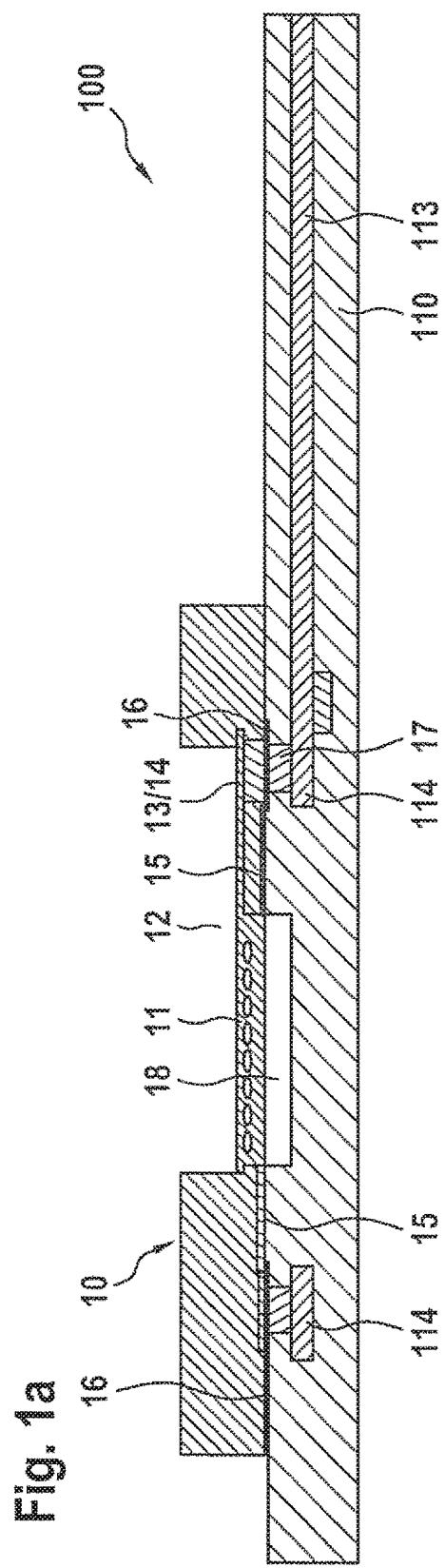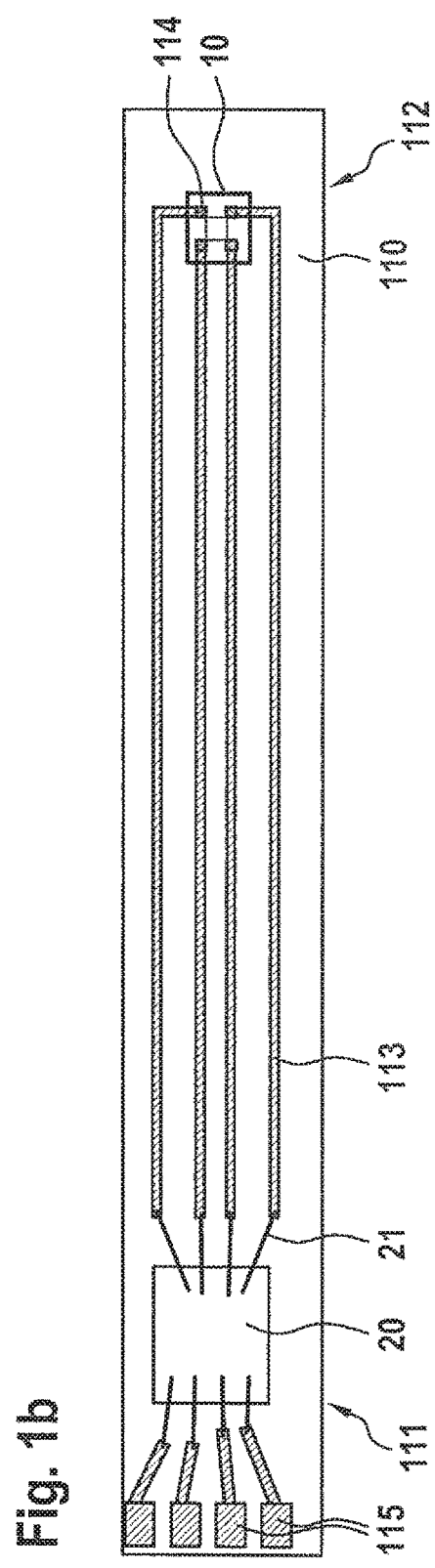

COMPONENT PART HAVING A MECS COMPONENT ON A MOUNTING CARRIER

CROSS REFERENCE

The present application claims the benefit under 35 U.S.C. § 119 of German Patent Application No. DE 102015209267.4 filed on May 21, 2015, which is expressly incorporated herein by reference in its entirety.

BACKGROUND INFORMATION

The present invention relates to a component part which includes at least one micro-electrochemical sensor (MECS) component and a carrier for mounting and electrically contacting the MECS component on an application circuit board. A diaphragm is developed in the layer structure of the MECS component, which spans an opening in the rear side of the component substrate.

MECS components, for example, are used within the framework of gas sensors in the automotive sector, but also for applications that lie outside the automotive field. Of great importance is the use of MECS components as lambda probes for the purpose of ascertaining the oxygen concentration in the exhaust gas flow of internal combustion engines and heating systems. In such cases the MECS component is usually exposed to very high temperatures and a chemically highly aggressive measuring environment.

SUMMARY

The present invention provides a packaging technology for MECS components, which allows the realization of extremely robust components which are resistant to high temperatures and media.

According to the present invention, this may be achieved by bonding the MECS component to the carrier using flip chip technology, so that a hermetically tight mechanical connection exists between the top surface of the MECS component and the carrier surface in at least one connection region, and an electric connection exists between the MECS component and the carrier in at least one contact area.

In the example packaging according to the present invention, the measuring medium is acting on the rear side of the MECS component or the rear side of the diaphragm of the MECS component, while at least regions of the front side of the MECS component do not make contact with the measuring medium because of the connection with the carrier or are at least protected from adverse effects of the measuring environment for the most part. In addition, regions of the carrier surface are shielded from the measuring medium as well as a result of the connection between the MECS component and the carrier.

The layout of the hermetically sealed bond between the MECS component and the carrier defines the surface regions of the MECS front side and the carrier front side that are completely cut off from the measuring medium. This makes it possible to selectively protect the diaphragm region that includes the circuit elements for the measured-value acquisition on the MECS-side. Moreover, it is advantageous if the bonding points between the MECS component and the carrier that function as electrical connections are shielded from the measuring medium as well. Toward this end, at least one connection area is designed to be circumferentially sealed, so that it surrounds the diaphragm and the at least one contact area. Given an appropriate layout of the carrier, for instance, even circuit components of an evaluation circuit that are integrated on the carrier are thereby able to be protected from the measuring medium.

In one preferred specific embodiment of the present invention, the coefficient of thermal expansion of the substrate materials of the MECS component and the carrier are adapted to each other.

This makes it possible to avoid thermally induced mechanical tensions in the component structure that result in a falsification of the measured value. This may play an important role especially in high-temperature applications.

A precondition for the packaging according to an example embodiment of the present invention is a carrier substrate which can be connected to the MECS topside in a hermetically tight manner by a bonding method and allows the realization of contact pads and plated-through holes or buried circuit tracks for the electrical contacting of the MECS component. Especially suitable as a carrier substrate is a multilayer ceramic circuit board provided with a bondable surface. In the case of MECS components that are realized in silicon technology, it may be a glass ceramic, silicon or silicon-oxide surface. For one, the coefficient of thermal expansion of such a carrier is able to be adapted very well to the MECS component. For another, circuit tracks and/or plated-through holes can quite easily be integrated into the layer structure of such a carrier. The hermetically tight mechanical connection between carrier surface and MECS surface can simply be produced by anodic bonding or Si direct bonding in this case. In Si direct bonding, depending on the material of the surface layers, an Si—Si connection or an SiO2-SiO2 connection is produced.

However, it is also possible to use processed semiconductor wafers having an adapted coefficient of thermal expansion and a bondable surface layer, such as silicon wafers, silicon nitride carriers or cordierite ceramic carriers, as carrier substrate.

The electrical connection in the contact region is advantageously produced by thermal compression bonding using a high-fusion solder, a conductive bonding agent or a thick-film conductive paste. In this case the mechanical and the electrical connections can be produced in one process step.

For use in an aggressive measuring environment, in particular, it is advantageous if the exposed rear side of the MECS component and/or the exposed surface of the carrier are/is protected as well. Toward this end, these regions of the component surface may be provided with a passivation layer, such as Sol gel layers, as corrosion protection, or with a water-repellent layer for better thermal shock protection, and/or a non-stick layer to avoid deposits from the measuring environment.

The packaging according to an example embodiment of the present invention makes it possible to realize a hermetically tight sealed cavity between the diaphragm of the MECS component and the carrier. A reference gas may be enclosed in this cavity, which is advantageous for some applications, such as a lambda probe having a zirconium dioxide diaphragm. The construction of such a component will be discussed in more detail in the following text on the basis of the figures.

BRIEF DESCRIPTION OF THE DRAWINGS

As discussed above, there are various possibilities of embodying and further developing the teaching of the present invention in an advantageous manner. Reference is made to the description below of an exemplary embodiment of the present invention with reference to the figures.

FIG. 1a shows a schematic sectional view through a component 100 according to the present invention in the region of MECS component 10.

FIG. 1b shows a plan view of carrier 110 of component 100 fitted with components.

DETAILED DESCRIPTION OF EXAMPLE EMBODIMENTS

Component 100 described here includes a MECS component 10, which is configured as a μlambda probe, and an ASIC component 20 having an evaluation circuit for the μlambda probe. Both components 10 and 20 are mounted on a carrier 110, via which component part 100 is able to be fixed in place on an application circuit board and electrically contacted. The layout of carrier 110 and the positioning of components 10 and 20 on carrier 110 is explained below in greater detail in connection with FIG. 1b.

FIG. 1a illustrates the packaging of component part 100 in the region of MECS component 10. MECS component 10 is a silicon chip, in whose layer structure a diaphragm structure 11 is developed. It is made up of SiN hexagons assembled in the form of honeycombs, which form a frame structure for zirconium-dioxide diaphragms. Diaphragm structure 11 is coated with platinum and spans an opening 12 in the component's rear side.

Diaphragm structure 11 is electrically contacted via connection pads 14 on the component front side and via circuit tracks 13, which are likewise made of platinum here and which are buried in the layer construction of MECS component 10.

According to the present invention, MECS component 10 is bonded to carrier 110 using flip chip technology, i.e., face-down, and hermetically tight, mechanical as well as electrical connections between MECS component 10 and carrier 110 are produced in the process.

Carrier 110 in the exemplary embodiment described here is a multilayer ceramic circuit board having embedded circuit tracks 113. Such circuit boards, for example, are produced in thick-film technology. Through a suitable material selection for the individual layers, the coefficient of thermal expansion of circuit board 110 is able to be adapted very well to thermal coefficient of expansion of components 10, 20 to be placed on top, and in particular to the coefficient of thermal expansion of MECS component 10. In this production method, circuit tracks 113 are imprinted on a layer of circuit board 110 with the aid of a screen printing or stencil printing mask and then overprinted using a glass ceramic paste. In so doing, the regions of future connection pads 114 for the contacting of connection pads 14 are spared on MECS component 10, on the one hand, and a region underneath diaphragm 11 of MECS component 10, on the other, so that they are exposed on both sides even after mounting on carrier 110. As an alternative to the overprinting using a glass ceramic paste, circuit tracks 113 may also be covered by a glass ceramic foil provided with corresponding cut-outs, which is then laminated on top. This layer construction is then sintered under pressure in order to keep the lateral dimensions by the sinter shrinkage low. Carrier substrate 110 is then also planarized for the bonding process, for instance by polishing.

In the case of component 100 shown in FIG. 1a, both the hermetically sealed mechanical connections 15 and 16 and electrical connections 17 between MECS component 10 and carrier 110 were produced in one process step. In addition to anodic bonding and silicon direct bonding for hermetically tight mechanical connections 15 and 16, this process step also includes thermal compression bonding or ultrasonic bonding for electrical connections 17.

A first annular connection region 15 was produced circumferentially around diaphragm structure 11, which seals a cavity 18 between diaphragm structure 11 and carrier 110 in a hermetically tight manner. Oxygen as reference gas for the lambda probe measurement is situated in this cavity 18. Bonding connection 15 was produced between an annular, heavily doped silicon region or an annular platinum coating in or on the MECS surface and the carrier surface.

Using anodic bonding, a second annular, closed connection region 16 was produced in the outer edge region of MECS component 10. It surrounds not only diaphragm structure 11, but also electric connections 17, which are realized in the form of solder bumps from a temperature-stable alloy in this instance, such as Au, Pt, Pd, Ag and/or Ni, for example. These solder bumps were applied on metallized contact pads 14 of MECS component 10 and/or contact pads 114 of carrier 110 prior to mounting MECS component 10 on carrier 110. As an alternative, electrical connections 17 may also be realized in the form of conductive bonding agents or thick film conductive pastes, which are applied to the carrier surface by printing or dispensing before MECS component 10 is mounted. With the aid of the two hermetically tight, annular bonding connections 15 and 16, electrical connections 17 between MECS component 10 and carrier 110 were encapsulated, so that they are not only protected from the oxidizing oxygen reference gas in cavity 18 on the one hand, but also from the aggressive measuring environment of a lambda probe on the other.

The construction shown here may optionally also be provided with an non-stick layer on the exposed rear side of the MECS substrate and on the exposed carrier surface in order to keep the extent of deposits from the measuring environment on these component parts to a minimum and/or in order to reduce the effects of icing. For high-temperature applications, for example, non-stick layers made from SiC or SiN are suitable. At low temperatures at the installation location, silanization is another option.

The plan view onto carrier 110 of component 100 fitted with components shown in FIG. 1b illustrates that two mounting regions 111 and 112, which are spatially set apart from another and are consequently also thermally separated, are provided for components 10 and 20 in the layout of carrier 110. These mounting regions 111 and 112 are electrically interconnected via buried circuit tracks 113. ASIC component 20 is mounted in the "cold" region, and connected via wire bonds 21 to circuit tracks 113 on one side, and to electric connections 115 for the external electric contacting of component 100 on the other. To protect ASIC component 20 including bonding wires 21, this carrier region, for example, may be completely encapsulated in a molding mass and provided with a connector plug or cable.

On the opposite side of carrier 110 is the "hot" region which includes mounting region 112 for MECS component 10. Its mounting and electrical contacting was described in detail in the previous text in connection with FIG. 1a. Because of the packaging in the hot carrier region, component 100 according to the present invention is also suitable for use in the high-temperature region and in an aggressive measuring environment, such as the exhaust gas flow of an internal combustion engine.

What is claimed is:

1. A component, comprising:
   a micro-electrochemical sensor (MECS) component having a diaphragm which is developed in a layer construction on a substrate of the component and spans an opening in the substrate rear side, wherein the MECS component includes a material sensitive to a chemical in measuring medium; and a carrier for mounting and electrical contacting of the MECS component on an application circuit board, the MECS component being bonded to the carrier via flip chip technology so that a hermetically tight-mechanical connection between a top surface of the MECS component and a surface of the carrier exists at least in one connection region, and an electrical connection between the MECS component and the carrier exists in at least one contact area, wherein the hermetically tight mechanical connection includes:

a first hermetically tight connection that circumferentially surrounds the diaphragm, and a second hermetically tight connection that circumferentially surrounds an outer edge region of the MECS component.

2. The component as recited in claim 1, wherein at least one connection region is circumferentially closed and surrounds the diaphragm and the at least one contact region.

3. The component as recited in claim 1, wherein a cavity is situated between the diaphragm of the MECS component and the carrier, which is sealed in a hermetically tight manner by the bond connection between the MECS component and the carrier, and a reference gas is situated in the cavity.

4. The component as recited in claim 1, wherein the coefficient of thermal expansion of materials of the substrate of the MECS component and the carrier are such that the substrate of the MECS component and the carrier exhibit the same thermal expansion.

5. The component as recited in claim 1, wherein the carrier is a multilayer ceramic circuit board having a bondable one of: i) glass ceramic, ii) silicon, or iii) silicon-oxide surface, and the layer construction of the carrier includes at least one of circuit tracks and plated-through holes.

6. The component as recited in claim 1, wherein the mechanical connection in the connection region is produced by one of anodic bonding or silicon direct bonding.

7. The component as recited in claim 1, wherein the electrical connection in the contact region is produced by one of thermal compression bonding or ultrasonic bonding, one of using a high-fusion solder, or with the aid of a conductive bonding agent or a thick-film conductive paste.

8. The component as recited in claim 1, wherein at least one of an exposed rear side of the MECS component, and an exposed surface of the carrier, is provided with at least one of a passivation layer, a water-repellent layer, and a non-stick layer.

9. The component as recited in claim 1, wherein the MECS component is a µlambda probe having a zirconium-dioxide diaphragm.

10. The component as recited in claim 1, wherein the second hermetic connection circumferentially surrounds the electrical connection.

11. The component as recited in claim 1, wherein:

a first surface of the electrical connection directly contacts the second hermetic connection, and a second surface of the electrical connection that is opposite the first surface directly contacts an electrical contact pad embedded in a material of the carrier.

* * * * *